United States Patent [19]
Sharma

[11] Patent Number: 6,121,366
[45] Date of Patent: Sep. 19, 2000

[54] THIN-WALLED RUBBER ARTICLES WITH WALLS HAVING A RELATIVELY LOW MODULUS

[75] Inventor: Pam Sharma, Montreal, Canada

[73] Assignee: ECI Medical Technologies Inc., Bridgewater, Canada

[21] Appl. No.: 09/032,543

[22] Filed: Feb. 26, 1998

Related U.S. Application Data

[63] Continuation-in-part of application No. 08/786,240, Jan. 21, 1997, abandoned.

[51] Int. Cl.$^7$ ....................................................... C08K 5/01
[52] U.S. Cl. ........................... 524/487; 524/488; 524/505; 525/89; 525/98; 525/99; 525/314
[58] Field of Search ..................................... 524/487, 488, 524/505; 525/89, 98, 99, 314

[56] References Cited

U.S. PATENT DOCUMENTS

| | | | |
|---|---|---|---|
| 3,933,723 | 1/1976 | Grenness | 260/33.6 A |
| 5,112,900 | 5/1992 | Buddenhagen et al. | 524/484 |
| 5,407,715 | 4/1995 | Buddenhagen et al. | 428/35.7 |
| 5,444,121 | 8/1995 | Grennes et al. | 525/89 |

FOREIGN PATENT DOCUMENTS

| | | | |
|---|---|---|---|
| 2112646 | 7/1994 | Canada | C08L 53/02 |
| 2134074 | 9/1994 | Canada | A41D 19/00 |
| 605381 | 1/1998 | European Pat. Off. | C08L 53/02 |

*Primary Examiner*—Peter D. Mulcahy
*Attorney, Agent, or Firm*—Schweitzer Cornman Gross & Bondell LLP

[57] ABSTRACT

A thin-walled rubber article with a relatively low modulus, prepared by dip forming, formed from a composition comprising styrene-isoprene-styrene (S-I-S) triblock copolymer, and styrene-butadiene-styrene (S-B-S) triblock copolymer with a S-I-S content in excess of at least 76% by weight. The composition additionally contains antiblocking agent to prevent the articles from sticking together, especially polyethylene wax. The articles are preferably gloves.

17 Claims, 4 Drawing Sheets

Figure 1: Tensile Strength - Non-Sterile Product

THIN-WALLED RUBBER ARTICLES WITH WALLS HAVING A RELATIVELY LOW MODULUS

This is a continuation-in-part of Ser. No. 08/786,240 filed Jan. 21, 1997 now abandoned.

FIELD OF THE INVENTION

The present invention relates to thin-walled rubber articles, such as gloves, condoms, and catheters which may be prepared by dip forming. Specifically, the invention relates to thin-walled rubber articles, the composition of the solution from which the thin-walled rubber articles may be prepared and the process of manufacture.

BACKGROUND TO THE INVENTION

Thin-walled, extensible articles such as gloves have been made from natural rubber compositions for a long time. In order to obtain articles having a sufficiently high strength and elasticity from natural rubber compositions, it is necessary to vulcanize or in other ways chemically cross-link the molecular chains of the rubber, which requires the presence of curing agents, activators and/or accelerators. The presence of such agents often gives rise to allergic reactions among the users of the articles. In addition, all latices of natural rubber contain proteins, which in extreme cases may cause allergic reactions e.g. swelling of a person's neck and air passageways. Such allergic reactions can result in fatal cases of anaphylactic shock. Surgeons, health care workers and other persons wearing the gloves are particularly susceptible, but patients are also vulnerable during surgical or other procedures, and the families of all such person can be subjected to airborne particles from clothing, hair or skin. In less extreme cases, other reactions occur, including hand dermatitis and hives.

As a result of the problems with gloves formed from latex-containing materials, efforts have been made to develop thin-walled rubber articles from synthetic polymers. In typical processes, articles made from synthetic polymers are manufactured from styrene block copolymers in a multiple-dip process that involves dipping a mould or former into solutions of the styrene block copolymers and drying the dip-coated mould between each dipping step. Such a process includes the use of starch powder. The powder is applied to the article following the final dip but prior to the stripping of the article from the mould or former. The powder acts to reduce surface tackiness and thus facilitates the donning of the glove.

U.S. Pat. Nos. 3,933,723 and 5,112,900 both relate to the use of solutions containing thermoplastic styrene-tri-block copolymers and plasticizers for the production of thin-walled rubber articles. Such solutions do not contain the proteins present in natural rubber i.e. the solutions are free of latex, and thus thin-walled rubber articles that are hypo-allergenic rubber articles may be obtained.

U.S. Pat. No. 5,444,121 relates to thin-walled rubber articles formed from a variety of compositions of styrene-isoprene-styrene (S-I-S) tri-block copolymers and styrene-butadiene-styrene (S-B-S) tri-block copolymers and, optionally, styrene-olefin-styrene (S-O-S) tri-block copolymers.

U.S. Pat. Nos. 5,112,900 and 5,407,715 describe the use of mixtures of styrene-ethylene/butylene-styrene (S-EB-S) tri-block copolymers in the manufacture of gloves.

Blends of styrene-butadiene block copolymers and styrene-isoprene block copolymers, including S-I-S and S-B-S tri-block copolymers, are disclosed for medical applications, including as gloves, in Canadian 2,112,646. Gloves made from a variety of polymers, including S-I-S and S-B-S tri-block copolymers, without the use of a solvent are disclosed in WO 94/20574.

Common to the solutions disclosed in the above-mentioned patents is the formation of a solid film which is understood to represent a physical cross-linking between the block copolymer molecules present in the solution. When the solvent evaporates, cross-linking is understood to occur between styrene domains of the molecular chains. This cross-linking eliminates the need to use the potential allergy-causing chemicals mentioned earlier. Furthermore, these solutions do not contain the proteins present in natural rubber and it is thus possible by using these solutions to prepare hypo-allergenic rubber articles.

The rubber articles disclosed in U.S. Pat. Nos. 3,933,723; 5,112,900; and 5,444,121 represent progressive developments in physical characteristics, specifically tensile strength and tear resistance. These characteristics are extremely important in providing barrier protection for the user. Unfortunately, the "fit-feel-comfort" qualities of the articles have not been optimized, which often results in premature fatigue, strain and discomfort on the part of the user. This quality is extremely important to rubber articles such as gloves which may be worn by a surgeon for several hours during an operation.

The aforementioned U.S. Pat. No. 5,444,121 reports that articles made from 100 percent styrene-isoprene-styrene (S-I-S) triblock copolymers were thin-walled and sticky, and the use of S-I-S in such rubber articles was limited to no more than 75 percent.

SUMMARY OF THE INVENTION

An object of an aspect of the present invention is to provide a rubber article with a significantly softer feel than previous patents by lowering the modulus and at the same time maintaining tensile strength.

Accordingly, the present invention provides a thin-walled, rubber article comprising styrene-isoprene-styrene (S-I-S) triblock copolymer, styrene-butadiene-styrene (S-B-S) triblock copolymer and optionally, styrene-olefin-styrene (S-O-S) triblock copolymer, and anti-blocking agent, wherein the S-I-S triblock copolymer is present in an amount of at least 76% by weight, the anti-blocking agent being selected in an amount such that unpowdered rubber articles pressed together and aged at 70° C. for 7 days (according to the procedure of ASTM D573-88) may be pulled apart.

In another aspect of the invention, there is provided a solution for the manufacture of gloves comprising styrene-isoprene-styrene (S-I-S) triblock copolymer, styrene-butadiene-styrene (S-B-S) triblock copolymer and optionally, styrene-olefin-styrene (S-O-S) triblock copolymer, and anti-blocking agent, in solvent, wherein the S-I-S triblock copolymer is present in an amount of at least 76% by weight, wherein the anti-blocking agent is selected in an amount such that unpowdered rubber articles pressed together and aged at 70° C. for 7 days (according to the procedure of ASTM D573-88) may be pulled apart.

DETAILED DESCRIPTION OF THE INVENTION

The present invention provides a thin-walled rubber article formed from a composition comprising a styrene-butadiene-styrene (S-B-S) triblock copolymer and a styrene-isoprene-styrene copolymer (S-I-S) with the latter comprising 76–100% by weight. Such a thin-walled rubber article may be fabricated by dipping a form in a blend comprising S-I-S triblock copolymer and S-I-S triblock copolymer, with a S-I-S content from 76–100% by weight, dissolved in a suitable solvent, removing the form from the solution, and allowing the solvent to evaporate. Such steps of dipping and allowing solvent to evaporate may be repeated until the rubber article has attained the desired wall-thickness.

In embodiments, the present invention relates to a method in which a mould (also known as a former), typically a mould in the form of a glove, is coated with styrene block copolymers dissolved in organic solvent. The styrene block copolymers for use in such a process are known, and are styrene-isoprene-styrene(S-I-S) tri-block copolymers, styrene-butadiene-styrene (S-B-S) tri-block copolymers, and optionally include styrene-olefin-styrene (S-O-S) tri-block copolymers. It may be particularly advantageous to use mixtures of such polymers. The amount of S-I-S tri-block copolymer may be varied from about 76% by weight to 100% by weight. Preferably the amount of S-I-S copolymer is at least 80% by weight, and especially 80–90% by weight.

As organic solvent for the styrene block copolymer, any inert solvent may be used. A solvent primarily consisting of aliphatic hydrocarbons is preferred, as vapours from aliphatic hydrocarbons tend to have lower toxicity than, for instance, halogen-containing or aromatic solvents. To obtain sufficiently high dissolution of the styrene block copolymer and good process characteristics, the solvent may advantageously contain a small amount of aromatic compounds, for instance up to 10% by weight of a solvent mainly consisting of aliphatic hydrocarbons may be aromatic compounds. It is furthermore preferred that the aliphatic hydrocarbons have a boiling point between 95° C. and 140° C. Depending on the particular blend of styrene block copolymers, the organic solvent is preferably used in amounts of 400–1200% by weight, based on the weight of styrene block copolymer.

It is to be understood that the solution for the preparation of a thin walled article according to the invention may have only one type of styrene block copolymer or a blend of different types of styrene block copolymers i.e. blends of styrene block copolymers of differing styrene contents. The composition of styrene block copolymers affecting the properties of the thin-walled articles that are obtained. Moreover, each type of styrene block copolymers may contain more than one variant of each type of styrene block copolymers e.g. of different viscosities, to attain a desired viscosity of the solution and/or to attain the desired mechanical properties of the thin-walled article. Thus, the solution may contain several variations of the same type of styrene block copolymers with different styrene contents and/or with different solution viscosities.

A particular tri-block copolymer e.g. S-I-S, may be characterized by the viscosity of a predetermined concentration in a solvent and the content of the end blocks in the tri-block copolymer. Thus, a S-I-S tri-block copolymer may be characterized by its solution viscosity in a 25% by weight solution in toluene at a specified temperature and by its styrene content. For instance, a preferred S-I-S tri-block copolymer has a styrene content of from 10–30% by weight and a solution viscosity of a 25% by weight solution of the copolymer in toluene at 25° C. of 0.5–5 Pa.s.

Examples of S-I-S tri-block copolymers are those sold under the name Kraton™ TR1107 or Kraton TR1111, which have styrene contents of 15% and 22% respectively, and solution viscosities in a 25% by weight solution in toluene at 25° C. of 1.6 and 1.4 Pa.s., respectively. Alternatively, the S-I-S tri-block copolymers may be of the type sold under the name Dexco™ 4111, which has a styrene content of about 18%, and a solution viscosity of a 25% by weight solution of the copolymer in toluene at 25° C. of 0.7–1.0 Pa.s.

Similarly, S-B-S tri-block copolymers with a range of solution viscosities may be used, for instance with a solution viscosity of a 25% by weight solution of copolymer in toluene at 25° C. of 0.5–30 Pa.s. The styrene content is preferably between 20 and 40% by weight. Examples of S-B-S tri-block copolymers include Kraton TR1101 with a styrene content of 31% by weight and a solution viscosity of a 25% by weight solution of copolymer in toluene at 25° C. of 4.0 Pa.s; Kraton TR1102 with a styrene content of 29% by weight and a solution viscosity of a 25% by weight solution of copolymer in toluene of 1.2 Pa.s., and Kraton 1184 with a styrene content of 30% by weight and a solution viscosity of a 25% by weight solution of copolymer in toluene at 25° C. of 20.0 Pa.s. Other examples of S-B-S tri-block copolymers are Dexco 2518 and Dexco 8508D. S-B-S tri-block copolymers typically have a very high modulus which results in an article with a low degree of elasticity but higher strength. The choice of solvent for dissolving the polymer material is based on its ability to form a completely stable and homogenous solution, and has been discussed above.

For the present invention, the content of S-B-S triblock copolymer is from 0–24% by weight of the blend of copolymers, and the remaining part is S-I-S triblock copolymer. A thin-walled rubber article prepared from such a copolymer blend has an exceptionally low modulus and good tensile strength; the latter characteristic comes as a surprise and contradicts what was expected based on the characteristics of S-I-S polymer.

A rubber article in accordance with the present invention, with a greater ozone resistance, may be provided by replacing a part of the S-B-S triblock copolymer by styrene-olefin-styrene (S-O-S) triblock copolymers. A polymerized olefin is saturated i.e. it contains no double bonds, and is therefore less sensitive towards ozone. Such a substitution makes it necessary that the solvent, apart from aliphatic hydrocarbons, contain a smaller level of aromatic hydrocarbons in order to attain the desired solution and in order to secure the development of a polymer matrix in which the various polymer chains form an interpenetrating molecular network.

Styrene-ethylene/butylene-styrene (S-EB-S) is one tri-block copolymer that may be used as the S-O-S triblock copolymer, preferably with a styrene content of 10–30% by weight and a solution viscosity in a 25% by weight solution in toluene at 25° C. of 1–10 Pa.s. The thin-walled rubber article according to this embodiment comprises S-B-S tri-block copolymer and S-EB-S triblock copolymer, with the requirement that at least 76% of the composition, by weight, be S-I-S triblock copolymer. The rubber article comprising S-EB-S triblock copolymer blend further preferably contains up to about 30% by weight of a naphthenic plasticizer, based on the copolymer blend.

In the present invention, the solution for the production of thin-walled rubber articles contains additives, such as antioxidants, release agents, and anti-blocking agents. Zinc dithiocarbamate is one example of a suitable antioxidant, present in quantities not greater than about 0.5 weight percent. Release agents, which are used to assist in mould release, may be of the modified fatty acid ester type e.g. oleamide, and are present in quantities typically not greater than 3.0 weight percent. Such additives are known. In addition, the solution contains anti-blocking agents to help prevent tackiness.

The anti-blocking agent is selected such that samples of the articles pressed together in the absence of powder and then heat aged at 70° C. for 7 days, may be peeled apart. The known anti-blocking agent paraffin wax that is typically used in amounts of 0.6 phr (pounds per hundred resin) e.g. at the 60% S-I-S composition disclosed herein, is not such an anti-blocking agent as the articles treated as above may not be peeled apart in the absence of use of powder. Acceptable anti-blocking agents include precipitated silica especially in amounts of at least 2.0 phr and polyethylene wax especially in amounts of 0.5–5.0 phr, preferably 1.–0–4.0 phr.

The preferred release agent is oleamide, in amounts of 0.225–0.45 phr. A release agent is normally used.

In a preferred embodiment of the method, the mould is dip-coated with the organic solution of the styrene tri-block copolymers by dipping the mould into the solution. The solution is typically at temperatures in a range of about 28° C. to 32° C., with preferred temperatures being in the range of 29° C. to 31° C. The dip-coated mould is then removed from the solution and dried, usually dried in air at about 29–31° C. In a typical process, the mould is dip-coated more than once, and usually using a process that is operated continuously, i.e. the mould is dip-coated in a first solution, air dried, dip-coated in a second solution and air dried, and so forth, with the mould being suspended from a continuous belt so that it passes through the coating baths and through the air drying steps in sequence under controlled conditions. It is understood that the mould may be dip-coated a number of times e.g. up to at least four times, or more. The solutions in each coating bath used may be identical, or different solutions may be used e.g. solutions of different composition.

In a preferred embodiment of the invention, the rubber articles exhibit a tensile strength of at least 20 MPa.

In further preferred embodiments, the rubber articles are in the form of gloves, e.g. surgical or similar gloves.

Other features and advantages of the invention will be apparent from the following more detailed description of examples of the invention.

EXAMPLE I

Figure 1:
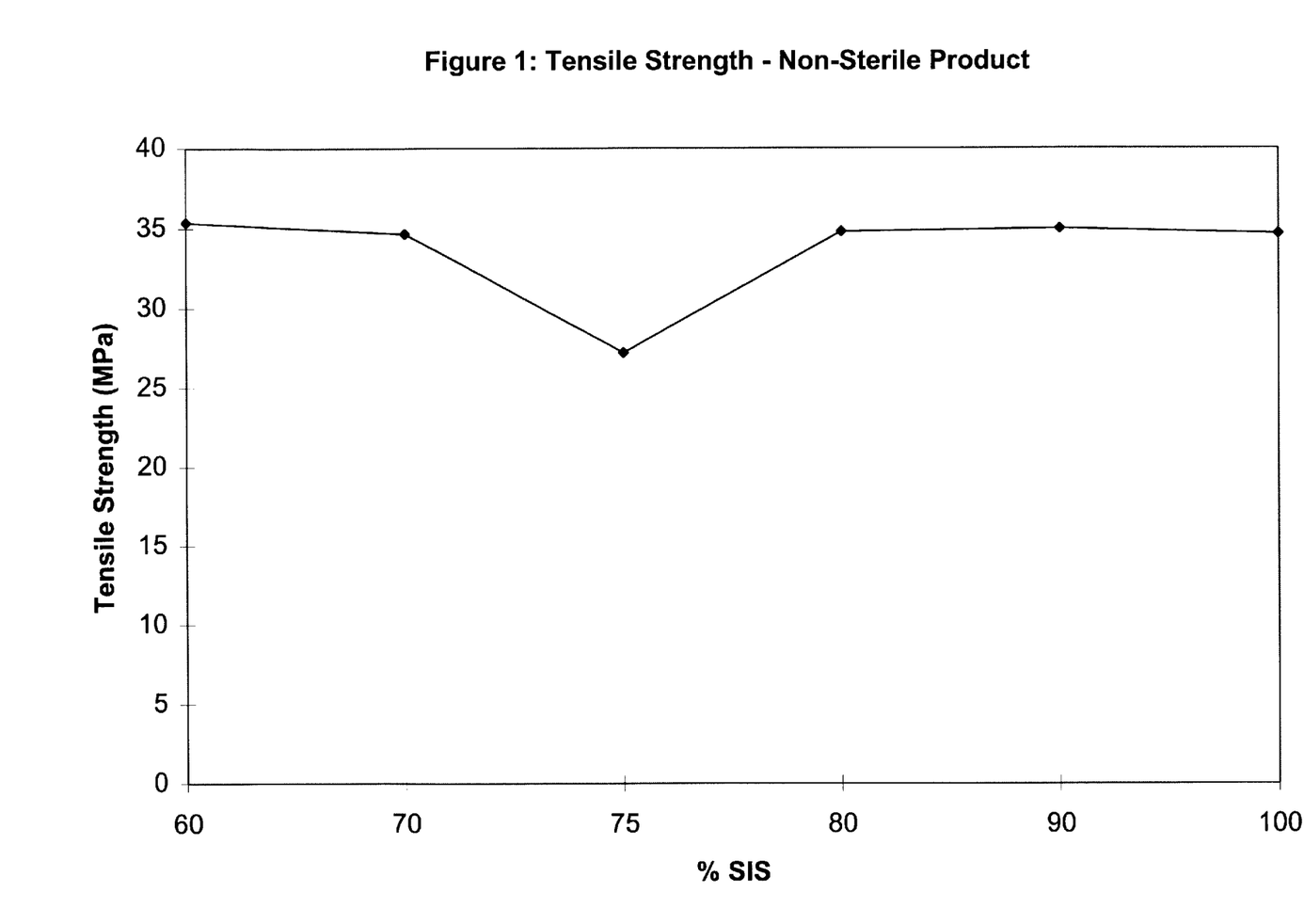
FIG. 1 is a plot of tensile strength for test compositions of varying S-I-S percentages in non-sterile, non-aged samples of Example I.

A test solution in accordance with the present invention was prepared by dissolving a blend of S-I-S and S-B-S triblock copolymers in the amounts given in the abscissa of FIG. 1 using an aliphatic hydrocarbon solvent with a boiling point from 95° to 140° C. The S-I-S copolymer sold under the name DEXCO 4111 has been found to be particularly well suited for the present invention, providing results strongly unexpected in view of the prior art. Small quantities of an antioxidant, release agent and anti-blocking agent were added based on the total copolymer weight.

Test specimens were prepared on a miniature dipping apparatus by dipping several hand-shaped forms in the described solution and then slowly removing them from the solution while rotating. The objective was to form a uniform layer of the solution as it adhered to the forms. The forms with the adhered solution were then air-dried at room temperature to evaporate the solvent from the thin elastomeric layer. This process was repeated until the rubber articles had obtained the desired wall-thickness.

Figure 2:
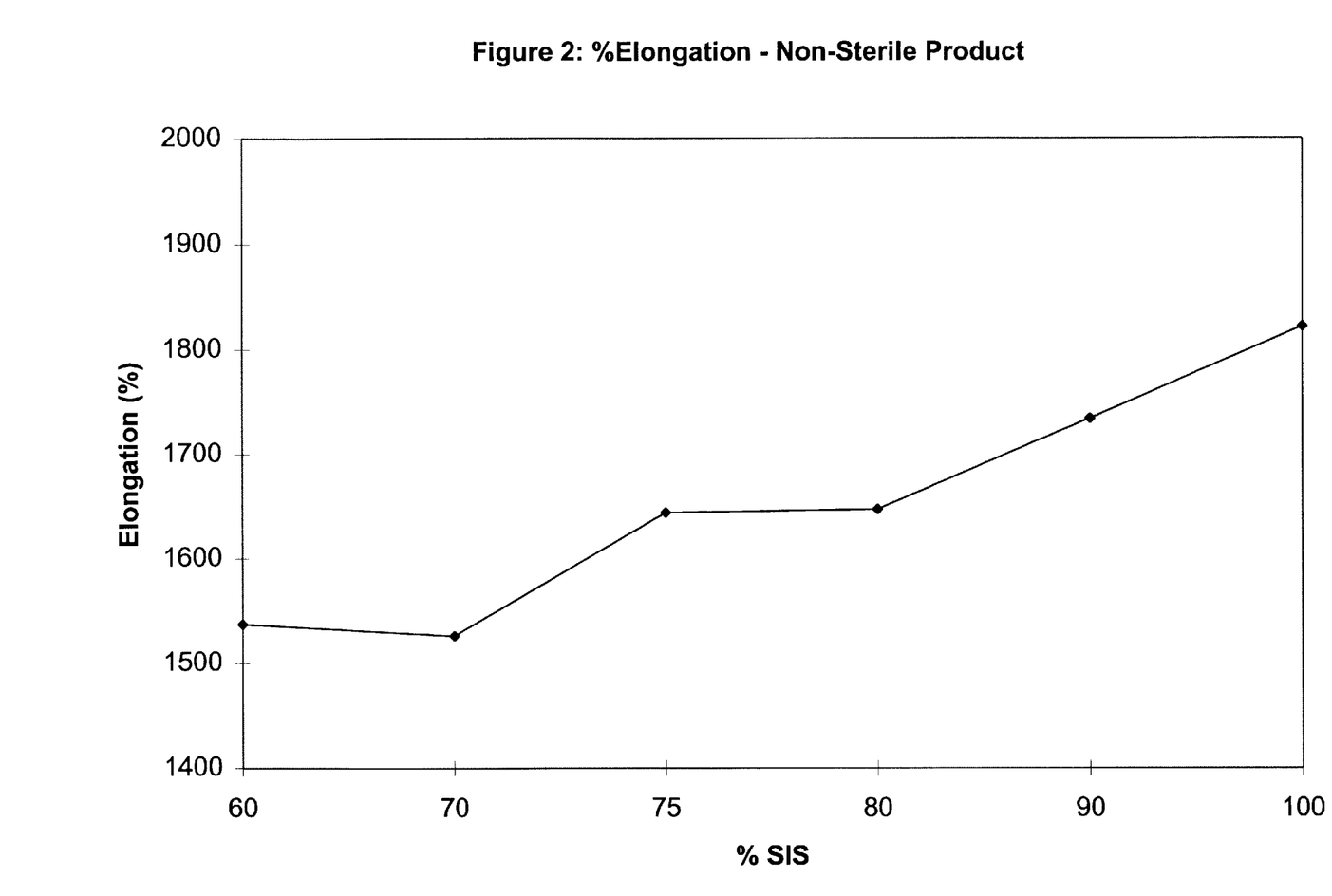
FIG. 2 is a plot of ultimate elongation of samples of FIG. 1.

The observed relationship between S-I-S content and physical characteristics is unexpected for the range and polymer tested. From FIG. 1, it can be seen that, as expected, the tensile strength decreased as the S-I-S content approached 75 percent; however, beyond this value, the tensile strength increased and then remained consistent. Similarly, FIG. 2 demonstrates a change in ultimate elongation properties around the 75 percent S-I-S mark. One would not anticipate this change in elongation, but rather would expect the elongation to continually increase with increasing S-I-S content. This is contrary to the teachings of U.S. Pat. No. 5,444,121.

Figure 3:
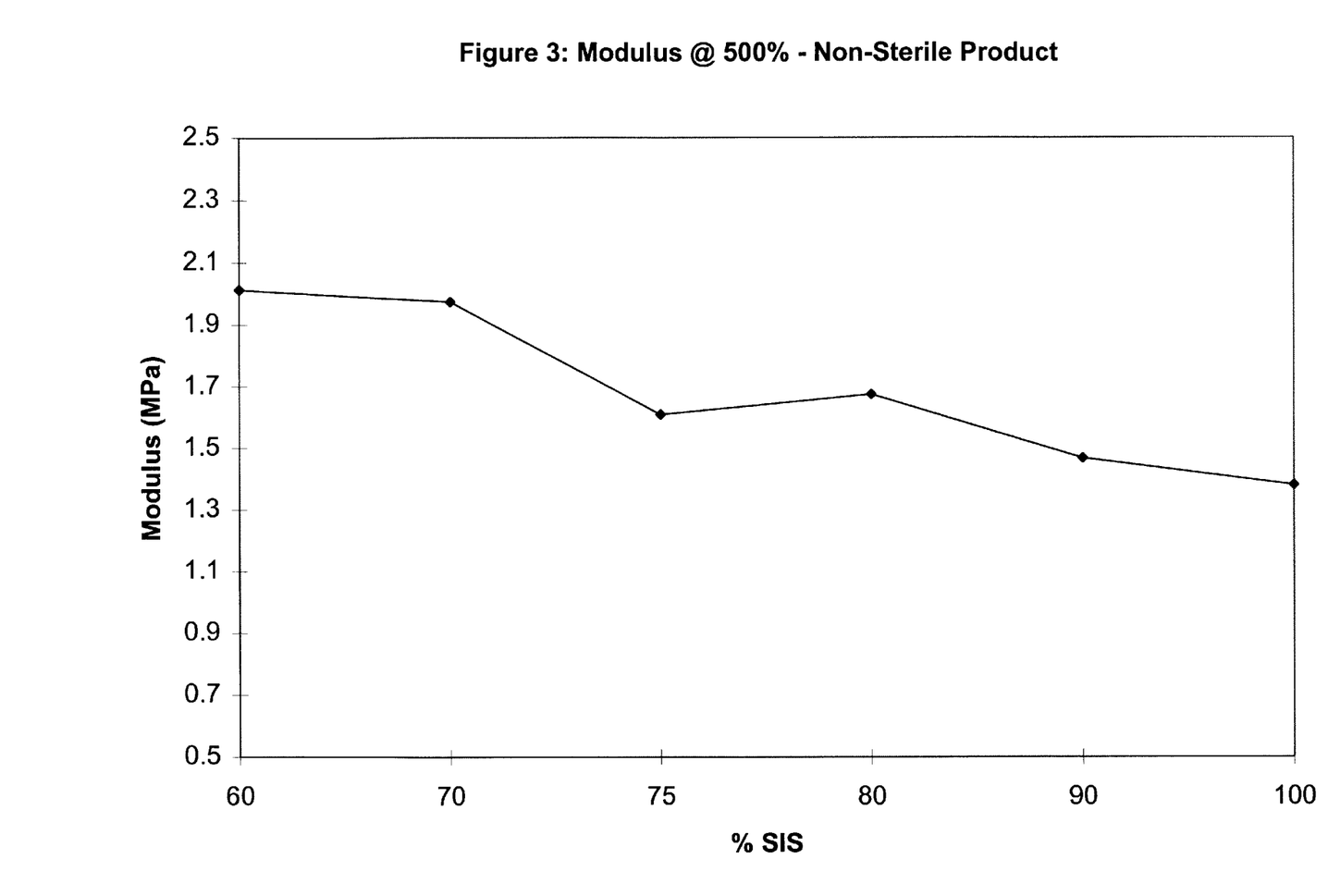
FIG. 3 is a plot of modulus at an elongation of 500% of samples of FIG. 1.

The primary objective of achieving a low modulus was met by increasing the S-I-S content beyond 75 percent, as can be seen in FIG. 3. In going from 75 to 100 percent S-I-S, the modulus dropped by over 30 percent.

Figure 4:
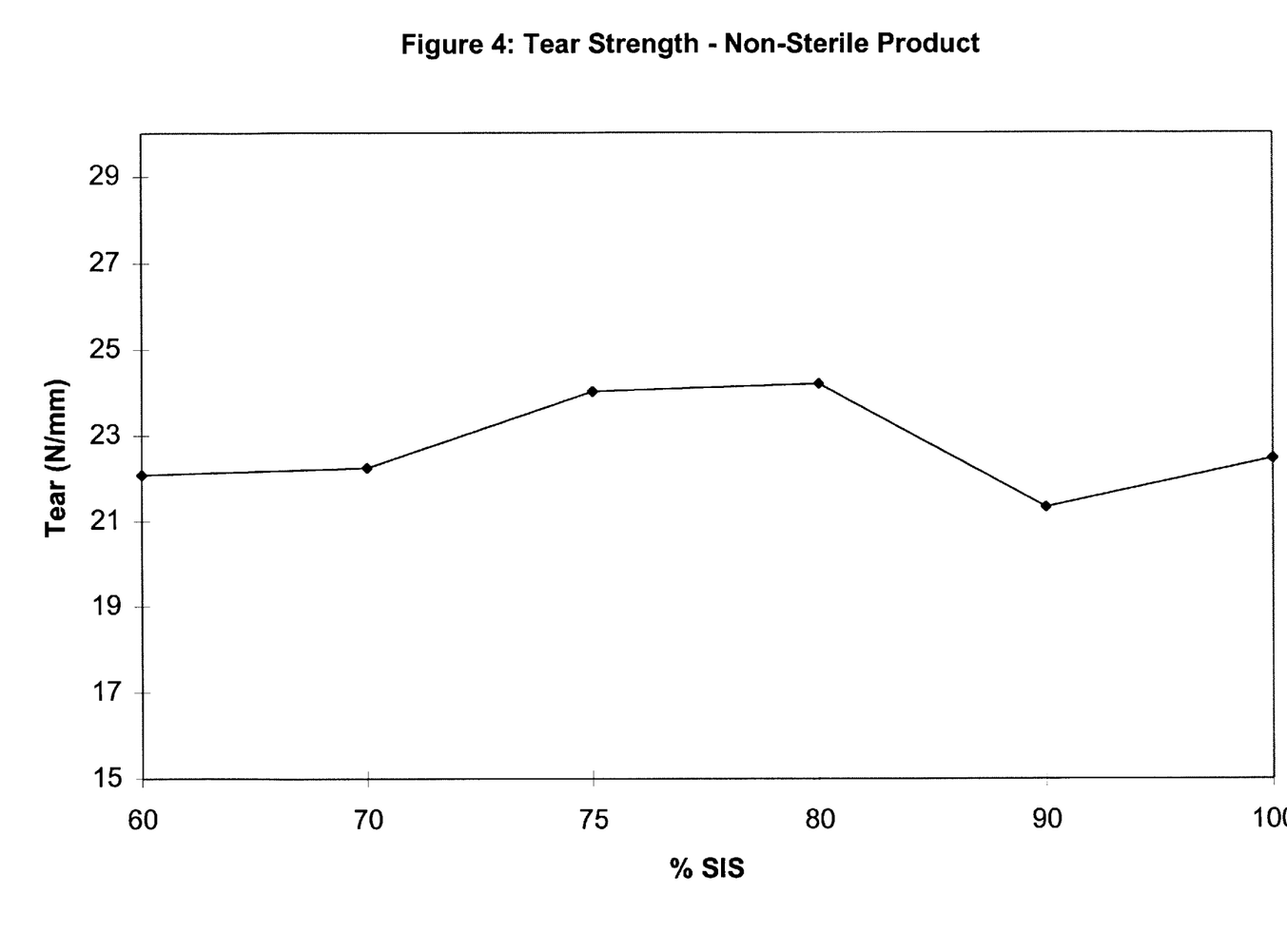
FIG. 4 is a plot of tear resistance of samples of FIG. 1.

Tear resistance remains essentially unchanged with change in S-I-S content, as shown in FIG. 4. These figures indicate the unexpected results that it is possible to produce a rubber article with a much lower modulus by increasing the S-I-S percentage without losing the tensile strength characteristics of the article. In addition, the tackiness observed and as expected with reference to the prior art with higher S-I-S content can be overcome through the use of anti-blocking agents as described previously.

TEST METHODS

Tests for all physical properties except tear resistance were performed using ASTM D412 (92). Tear resistance was determined using ASTM 624 and a Die C 90° angle cutter. All tests were performed on an Instron 4465 tensile machine. All test results surpassed the minimum standards specified under ASTM D3577-88 and ASTM D3578-88 for rubber gloves.

EXAMPLE II

A series of compositions were formed from a styrene-isoprene-styrene (S-I-S) triblock copolymer and styrene-butandiene-styrene (S-B-S) triblock copolymer in which the amount of S-I-S component was varied. The compositions were as follows:

A) 60% Dexco 4111 (S-I-S) triblock copolymer, 14% Dexco 8508D (S-B-S) triblock copolymer and 26% Dexco 2518 (S-B-S) triblock copolymer;

B) 76% Dexco 4111 (S-I-S) triblock copolymer, 14% Dexco 8508D (S-B-S) triblock copolymer and 10% Dexco 2518 (S-B-S) triblock copolymer;

C) 80% Dexco 4111 (S-I-S) triblock copolymer, 5% Dexco 8508D (S-B-S) triblock copolymer and 15% Dexco 2518 (S-B-S) triblock copolymer;

D) 90% Dexco 4111 (S-I-S) triblock copolymer, 0% Dexco 8508D (S-B-S) triblock copolymer and 10% Dexco 2518 (S-B-S) triblock copolymer; and E) 100% Dexco 4111 (S-I-S) triblock copolymer, 0% Dexco 8508D (S-B-S) triblock copolymer and 0% Dexco 2518 (S-B-S) triblock copolymer.

The compositions additionally contain 0.6 phr (pounds per hundreds resin) of paraffin wax, 0.225 phr of oleamide release agent and 0.4 phr of carbamate antioxidant.

Gloves were made using each of the compositions using the procedure described herein. The resultant gloves had a thickness of 0.32–0.36 mm at the cuff.

The gloves were subjected to a variety of physical test procedures. In each test, the sample size was ten gloves. In the results reported below, the standard deviation is shown in brackets.

The gloves were of four different categories, as follows:
(i) non-aged/non-sterile gloves,
(ii) aged/non-sterile gloves,
(iii) non-aged/sterile gloves, and
(iv) aged/sterile gloves.

obtained could be opened for testing. In the absence of cornstarch, the gloves with 100% S-I-S copolymer would not be openable even with the presence of the release agents, but it is believed that other gloves would exhibit less stickiness with decreasing S-I-S content.

In the Tables herein, the following are the units of measurements unless specified otherwise:

Tensile Strength reported in Mpa

Ultimate Elongation in percent

Modulus at 500% elongation in Mpa

Tear Strength in N/mm

Force at Break in N

The results obtained were as follows:

TABLE I

| % SIS | Non-Aged/Non-Sterile | Aged/Non-Sterile | Non-Aged/Sterile | Aged/Sterile |
|---|---|---|---|---|
| TENSILE STRENGTH | | | | |
| 60 | 32.11 (2.39) | 33.08 (3.51) | 24.96 (1.46) | 27.39 (2.54) |
| 76 | 27.52 (2.34) | 27.97 (2.22) | 18.33 (1.66) | 21.91 (1.27) |
| 80 | 30.35 (3.01) | 27.95 (3.85) | 23.80 (2.67) | 25.50 (3.02) |
| 90 | 28.98 (3.63) | 26.85 (3.52) | 26.80 (2.42) | 24.71 (2.55) |
| 100 | 25.94 (5.70) | 27.58 (3.28) | 23.53 (2.69) | 21.60 92.80 |
| ASTM 3577 | 21 (min.) | 16 (min.) | 17 (min.) | 12 (min.) |
| ULTIMATE ELONGATION | | | | |
| 60 | 1403 (33) | 1421 (55) | 1504 (50) | 1454 (42) |
| 76 | 1492 (74) | 1536 (45) | 1554 (58) | 1600 (51) |
| 80 | 1502 (47) | 1480 (39) | 1582 (39) | 1552 (64) |
| 90 | 1628 (56) | 1526 (41) | 1607 (55) | 1509 (34) |
| 100 | 1552 (53) | 1585 (54) | 1585 (77) | 1536 (45) |
| ASTM 3577 | 700 (min.) | 500 (min.) | 650 (min.) | 490 (min.) |
| MODULUS AT 500% ELONGATION | | | | |
| 60 | 1.971 (0.087) | 2.029 (0.073) | 1.803 (0.075) | 1.947 (0.077) |
| 76 | 1.680 (0.097) | 1.764 (0.057) | 1.631 (0.062) | 1.745 (0.060) |
| 80 | 1.629 (0.083) | 1.653 (0.085) | 1.570 (0.057) | 1.649 (0.036) |
| 90 | 1.430 (0.040) | 1.620 (0.031) | 1.488 (0.051) | 1.562 (0.051) |
| 100 | 1.337 (0.061) | 1.416 (0.030) | 1.291 (0.071) | 1.313 (0.041) |
| ASTM 3577 | N/A | N/A | N/A | N/A |
| TEAR STRENGTH | | | | |
| 60 | 22.64 (0.91) | 21.57 (1.17) | 23.54 (1.18) | 21.81 (1.57) |
| 76 | 26.10 (1.04) | 23.86 (1.12) | 23.19 (1.49) | 22.31 (1.42) |
| 80 | 23.65 (2.28) | 23.70 (2.76) | 22.77 (2.60) | 21.69 (1.55) |
| 90 | 23.28 (1.00) | 23.01 (1.36) | 23.67 (1.00) | 23.57 (1.36) |
| 100 | 23.29 (1.74) | 22.67 (0.17) | 23.34 (2.84) | 23.60 (3.17) |
| FORCE AT BREAK | | | | |
| 60 | 17.68 (1.29) | 20.98 (3.46) | 14.58 (1.01) | 16.01 (1.63) |
| 76 | 16.64 (1.79) | 19.68 (2.25) | 11.63 (1.31) | 14.41 (0.09) |
| 80 | 18.46 (1.22) | 17.76 (2.83) | 14.80 (2.03) | 15.52 (1.50) |
| 90 | 19.39 (2.62) | 17.69 (2.58) | 17.53 (1.61) | 15.55 (0.95) |
| 100 | 14.18 (3.00) | 15.56 (2.04) | 12.92 (1.43) | 12.98 (1.29) |
| EN455-2 | 3 | 3 | 7.5 | 5.5 |

Gloves were aged using the procedure of ASTM D-573-88, in which the gloves are aged for a period of seven days at 70° C. Gloves were sterilized by subjecting to gamma radiation in an amount in the range of 25–50 kGy's.

In the results, the applicable ASTM or European (EN) standard specifications for gloves have been included. Gloves must meet or exceed the specifications to be commercially acceptable. However, tear test results are not a specification required for commercial acceptability of gloves.

All gloves were powdered externally with approximately 1% cornstarch prior to removal from the mould to prevent sticking between the external glove surfaces. The gloves The results for sterile non-aged samples are believed to be the most relevant to use of the glove, as that is the form of the gloves as would be used, e.g. by a surgeon. It was found that a substantial increase in tensile strength was obtained as the S-I-S triblock copolymer content increased from 76% to 100%. The trend of decreasing values from 60% S-I-S to the value of 76% S-I-S that is marginally above the standard of ASTM 3577 was substantially reversed in the compositions at higher S-I-S content.

Ultimate elongation and tear strength remained at high values. Modulus decreased, indicating that softer gloves were obtained.

EXAMPLE III

The procedure of Example II was repeated using composition C i.e. the composition containing 80% S-I-S triblock co-polymer component. In a series of compositions the additives added to the composition were varied, as follows:

F. 0.5 phr Carbamate*/0.6 phr Paraffin*;
G. 0.5 phr Santowhite*/0.6 phr Paraffin;
H. 0.5 phr Carbamate/2.0 phr HiSil*;
I. 0.5 phr Carbamate/5.0 phr Polyethylene Wax*;
J. 0.5 phr Santowhite/2.0 phr HiSil; and
K. 0.5 phr Santowhite/5.0 phr Polyethylene Wax.

* zinc dithiocarbamate;
Santowhite™ antioxident from Flexsys;
Paraffin wax;
HiSil 233 precipitated silica from PPG Industries Inc.;
S394-N1 polyethylene wax (Shamrock Technologies Inc.)
Gloves were fabricated and tested using the procedure of Example II.

The test results obtained were as follows:

The compositions were tested for anti-blocking properties by casting films, which were allowed to dry at ambient temperature for about 24 hours. The films were then further dried in a forced air oven at 110° C. for 5 minutes, and allowed to equilibrate to ambient temperature. The films were cut into strips measuring 2×5 inches and laminated together, by hand pressing, to represent external glove surfaces. No powder was used. The laminated (pressed) strips were aged at 70° C. for 7 days, using the procedure of ASTM D573-88.

Blocking of the laminated strips was subjectively assessed as follows:

0 =film surfaces do not demonstrate sticking;
1 =film surfaces demonstrate minor sticking but may be peeled apart;
2 =film surfaces demonstrate excessive sticking and cannot be peeled apart.

TABLE II

| % SIS | Non-Aged/Non-Sterile | Aged/Non-Sterile | Non-Aged/Sterile | Aged/Sterile |
|---|---|---|---|---|
| TENSILE STRENGTH (MPA) | | | | |
| F | 29.79 (2.76) | 28.08 (3.16) | 22.17 (1.59) | 17.61 (1.05) |
| G | 29.43 (3.06) | 28.26 (4.47) | 23.46 (0.95) | 19.10 (1.37) |
| H | 23.60 (3.02) | 26.68 (4.11) | 23.00 (1.83) | 20.93 (1.66) |
| I | 30.33 (2.03) | 26.92 (3.74) | 24.56 (2.57) | 21.23 (1.80) |
| J | 28.80 (2.60) | 18.37 (4.98) | 23.11 (1.93) | 18.27 (1.55) |
| K | 23.16 (4.37) | 23.38 (5.31) | 22.68 (3.30) | 20.55 (1.33) |
| ASTM 3577 | 21 (min.) | 16 (min.) | 17 (min.) | 12 (min.) |
| ULTIMATE ELONGATION (%) | | | | |
| F | 1527 (54) | 1498 (36) | 1520 (54) | 1518 (58) |
| G | 1483 (74) | 1479 (49) | 1495 (53) | 1531 (62) |
| H | 1410 (36) | 1825 (54) | 1407 (68) | 1503 (39) |
| I | 1522 (42) | 1485 (47) | 1561 (55) | 1614 (32) |
| J | 1301 (49) | 1273 (79) | 1351 (39) | 1468 (92) |
| K | 1442 (69) | 1387 (61) | 1555 (65) | 1572 (46) |
| ASTM 3577 | 700 (min.) | 500 (min.) | 650 (min.) | 490 (min.) |
| MODULUS @ 500% ELONGATION (Mpa) | | | | |
| F | 1.776 (0.065) | 1.726 (0.071) | 1.621 (0.053) | 1.647 (0.059) |
| G | 1.794 (0.054) | 1.814 (0.078) | 1.746 (0.075) | 1.669 (0.045) |
| H | 1.747 (0.057) | 1.797 (0.055) | 1.829 (0.029) | 1.707 (0.045) |
| I | 1.731 (0.059) | 1.782 (0.043) | 1.632 (0.152) | 1.659 (0.067) |
| J | 1.994 (0.056) | 1.858 (0.086) | 1.912 (0.075) | 1.705 (0.064) |
| K | 1.697 (0.069) | 1.710 (0.051) | 1.547 (0.064) | 1.623 (0.075) |
| ASTM 3577 | N/A | N/A | N/A | N/A |
| FORCE @ BREAK | | | | |
| F | 16.52 (1.34) | 18.12 (2.11) | 13.02 (0.72) | 10.58 (0.79) |
| G | 17.80 (2.23) | 18.84 (2.86) | 14.10 (0.52) | 11.90 (1.22) |
| H | 14.24 (1.96) | 18.95 (3.26) | 13.70 (1.02) | 13.70 (1.14) |
| I | 18.74 (1.38) | 19.31 (2.70) | 15.63 (1.36) | 15.51 (0.90) |
| J | 13.88 (1.36) | 11.78 (3.30) | 13.79 (1.39) | 11.96 (1.63) |
| K | 14.53 (3.01) | 14.04 (3.76) | 15.59 (2.31) | 13.82 (1.16) |
| EN455-2 | 3 | 3 | 7.5 | 5.5 |

EXAMPLE IV

Compositions of 80% by weight of S-I-S triblock copolymer according to Composition C of Example II were prepared. Each composition contained 0.225 phr of oleamide, which is a release agent, and an anti-blocking agent. The anti-blocking agents tested were paraffin wax, S-394-N1 polyethylene wax from Shamrock Technologies Inc. and HiSil™ 233 precipitated silica from PPG Industries Inc.

The results obtained were as follows:

TABLE III

| Film | Anti-block Additive | Concentration (phr) | Blocking Level |
|---|---|---|---|
| 1 | paraffin wax | 0.6 | 2 |
| 2 | polyethylene wax | 0.5 | 1 |

TABLE III-continued

| Film | Anti-block Additive | Concentration (phr) | Blocking Level |
|---|---|---|---|
| 3 | polyethylene wax | 2.0 | 1 |
| 4 | polyethylene wax | 5.0 | 1 |
|   | silica | 0.5 | 2 |
| 6 | silica | 1.5 | 2 |
| 7 | silica | 2.5 | 1 |
| 8 | polyethylene wax/silica | 0.5/0.5 | 1 |
| 9 | polyethylene wax/silica | 0.5/1.5 | 0 |
| 10 | polyethylene wax/silica | 0.5/2.5 | 0 |
| 11 | polyethylene wax/silica | 2.0/0.5 | 1 |
| 12 | polyethylene wax/silica | 2.0/1.5 | 0 |
| 13 | polyethylene wax/silica | 2.0/2.5 | 0 |
| 14 | polyethylene wax/silica | 5.0/0.5 | 1 |
| 15 | polyethylene wax/silica | 5.0/1.5 | 0 |
| 16 | polyethylene wax/silica | 5.0/2.5 | 1 |

Silica has a tendency to settle from solution, and steps to counteract this effect might be required.

Polyethylene wax, alone or in combination with silica, was the preferred anti-blocking agent.

What is claimed is:

1. A thin-walled, rubber article comprising styrene-isoprene-styrene (S-I-S) triblock copolymer, styrene-butandiene-styrene (S-B-S) triblock copolymer and anti-blocking agent, wherein the S-I-S triblock copolymer is present in an amount greater than 76% by weight of total triblock copolymer, the anti-blocking agent being selected in an amount such that unpowdered rubber articles pressed together and aged at 70° C. for 7 days (according to the procedure of ASTM D573-88) may be pulled apart.

2. A rubber article according to claim 1, in which the S-I-S triblock copolymer has a styrene content of from 10–30% by weight and a solution viscosity in a 25% by weight solution in toluene at 25° C. of 0.5–5 Pa.s.

3. A rubber article according to claim 2 in the form of a glove.

4. A rubber article according to claim 3, in which the anti-blocking agent is polyethylene wax.

5. A rubber article according to claim 4, in which the S-B-S triblock copolymer has a styrene content of from 20 to 40% by weight and a solution viscosity in a 25% by weight solution in toluene at 25° C. of 0.5–30 Pa.s.

6. A rubber article according to claim 3 further comprising release agents in an amount not exceeding 3.0% by weight of total triblock copolymer, antioxidants in an amount not exceeding 0.5% by weight of total triblock copolymer and said anti-blocking agents in an amount not exceeding 5.0% by weight of total triblock copolymer.

7. A rubber article according to claim 6 comprising S-I-S triblock copolymer, S-B-S triblock copolymer and styrene-olefin-styrene (S-O-S) triblock copolymer.

8. A rubber article according to claim 7 in which the anti-blocking agent is polyethylene wax.

9. A rubber article according to claim 4 in which the S-I-S content is at least about 80% of the total triblock copolymer weight.

10. A rubber article according to claim 4 in which the S-I-S content is in the range of about 80–90% by total triblock copolymer weight.

11. A rubber article according to claim 4 in which the amount of antiblocking agent is 3–5% by total copolymer weight.

12. A rubber article according to claim 3 in which non-aged sterile articles exhibit a tensile strength of at least 20 MPa.

13. A rubber article according to claim 4 in which non-aged sterile articles exhibit a tensile strength of at least 20 MPa.

14. A solution for the manufacture of rubber article comprising styrene-isoprene-styrene (S-I-S) triblock copolymer, styrene-butadiene-styrene (S-B-S) triblock copolymer and optionally, styrene-olefin-styrene (S-O-S) triblock copolymer, and anti-blocking agent, in solvent, wherein the S-I-S triblock copolymer is present in an amount above 76% by weight of total triblock copolymer, the anti-blocking agent being selected in an amount such that unpowdered rubber articles pressed together and aged at 70° C. for 7 days (according to the procedure of ASTM D573-88) may be pulled apart.

15. A solution according to claim 14 in which the solution further comprises release agents in an amount not exceeding 3.0% by weight of total triblock copolymer, antioxidants in an amount not exceeding 0.5% by weight of total triblock copolymer and anti-blocking agents in an amount not exceeding 5.0% by weight of total triblock copolymer.

16. A solution according to claim 15 in which the solvent is a hydrocarbon solvent.

17. A method for the manufacture of gloves comprising dipping a mould in a solution of claim 14 and air drying the coated mould so obtained.

* * * * *